(12) United States Patent
Chou et al.

(10) Patent No.: US 8,133,226 B2
(45) Date of Patent: Mar. 13, 2012

(54) INTRAMEDULLARY FIXATION DEVICE FOR FRACTURES

(75) Inventors: Siaw Meng Chou, Singapore (SG); Beng Hai Lim, Singapore (SG); Cheng Hoe Desmond Tan, Singapore (SG)

(73) Assignees: Nanyang Technological University, Singapore (SG); Nanyang Polytechnic, Singapore (SG); National University Hospital, Singapore (SG); National University of Singapore, Singapore (SG)

( * ) Notice: Subject to any disclaimer, the term of this patent is extended or adjusted under 35 U.S.C. 154(b) by 903 days.

(21) Appl. No.: 11/996,568

(22) PCT Filed: Jul. 11, 2006

(86) PCT No.: PCT/SG2006/000192
§ 371 (c)(1),
(2), (4) Date: Jun. 25, 2008

(87) PCT Pub. No.: WO2007/008177
PCT Pub. Date: Jan. 18, 2007

(65) Prior Publication Data
US 2008/0294163 A1    Nov. 27, 2008

Related U.S. Application Data

(60) Provisional application No. 60/698,667, filed on Jul. 12, 2005.

(51) Int. Cl.
*A61B 17/72* (2006.01)

(52) U.S. Cl. ............................................. 606/63

(58) Field of Classification Search .............. 606/62–68, 606/254–263, 310, 313, 320, 325–328; 285/330–332.3
See application file for complete search history.

(56) References Cited

U.S. PATENT DOCUMENTS

| | | | |
|---|---|---|---|
| 3,986,504 A * | 10/1976 | Avila | 606/63 |
| 4,364,382 A | 12/1982 | Mennen | 128/92 D |
| 5,489,284 A | 2/1996 | James et al. | 606/62 |
| 5,531,792 A | 7/1996 | Huene | 623/16 |
| 5,534,004 A * | 7/1996 | Santangelo | 606/68 |
| 5,667,510 A | 9/1997 | Combs | 606/86 |
| 5,702,215 A | 12/1997 | Li | 411/21 |

(Continued)

FOREIGN PATENT DOCUMENTS

GB    2 269 108 A    2/1994

(Continued)

OTHER PUBLICATIONS

International Search Report and Written Opinion for PCT/SG2006/000192.

*Primary Examiner* — Eduardo C Robert
*Assistant Examiner* — Jerry Cumberledge
(74) *Attorney, Agent, or Firm* — Winston & Strawn LLP (57) ABSTRACT

An intramedullary fixation device for fractures having a core guide wire, and distal and proximal petal segments mountable on the core guide wire and being able to be moved towards each other. Each petal segment has multiple petals able to be expanded for gripping an internal wall of a medullary canal; expansion segments are also mountable on the core guide wire, each expansion segment having a tapered engagement surface for engaging with and expanding the petals of the distal and proximal petal segments. A corresponding method is also disclosed.

12 Claims, 8 Drawing Sheets

U.S. PATENT DOCUMENTS

| | | | | |
|---|---|---|---|---|
| 5,814,071 | A * | 9/1998 | McDevitt et al. | 606/232 |
| 6,575,973 | B1 * | 6/2003 | Shekalim | 606/62 |
| 2003/0039453 | A1 * | 2/2003 | Holmquist et al. | 385/86 |
| 2006/0229617 | A1 * | 10/2006 | Meller et al. | 606/62 |
| 2006/0241576 | A1 * | 10/2006 | Diederich et al. | 606/27 |
| 2006/0264951 | A1 * | 11/2006 | Nelson et al. | 606/72 |
| 2008/0262495 | A1 * | 10/2008 | Coati et al. | 606/62 |

FOREIGN PATENT DOCUMENTS

| | | |
|---|---|---|
| WO | WO 96/02201 | 2/1996 |

* cited by examiner

SECTION E-E
FIG. 11

FIG. 12

SECTION F-F
FIG. 13

FIG. 14

SECTION G-G
FIG. 15

INTRAMEDULLARY FIXATION DEVICE FOR FRACTURES

This application is a 371 filing of International Patent Application PCT/SG2006/000192, filed Jul. 11, 2006, which claims the benefit of application No. 60/698,667 filed Jul. 12, 2005.

FIELD OF THE INVENTION

This invention relates to a intramedullary fixation device of the type which includes distal and proximal petals, and expansion segments, mounted on a core guide wire and relates more particularly, though not exclusively, to such a device that is adjustable in length. More preferably, though not exclusively, the device can provide both torsional and longitudinal stability for fixing the fractured metacarpal bones, metatarsal bones in the foot and the phalanges of the fingers and toes, or bones of similar structure.

BACKGROUND OF THE INVENTION

Metacarpal and proximal phalangeal fractures are commonly encountered in hand fractures. The majority of these fractures can be treated non-operatively with good functional outcome. However, some unstable fractures with shortening or rotational deformities will require surgical intervention.

For all metacarpal fractures, proper fixation has always been the most important means for proper healing. There are many different types of fixation methods which are mainly in two categories—external and internal fixations. External fixation, usually by means of splints or casts, is used in cases in which the bone pieces are lined up well and surgery may not be necessary. However, some more complicated cases require operative treatment with insertion of an implant to fix the fracture. Ideally, a good internal fixation should have the merits of least exposure, least damage to soft tissue, and ease of manipulation.

There are generally four internal fixation methods currently used by clinicians for metacarpal fractures. They are Kirsches-wire (K wire) fixation, screw fixation, plate fixation, and pin fixation. Though these fixation methods have their own merits in dealing with different type of fractures, they have various shortcomings when applied to hand metacarpal fractures. Advantages of using K wires include minimal exposure and penetration of bone, short hospital stay, early mobilization, and few complications. However, it has the disadvantage of relatively weak fixation. Screw fixation can provide rigid compression loading of fracture site, but greater exposure is required for drilling. Plate fixation is designed to provide rigid internal fixation in order to facilitate early motion and thereby minimise joint and tendon complications. However the technique is demanding and secondary procedures are frequently required. A pin fixation is the insertion of a fixation pin into the medullary canal of a fractured metacarpal for stable bone fixation. The frequent complication rates emphasize the need for meticulous pin placement, adequate intraoperative evaluation of pin position, and satisfactory patient compliance.

So far there is no simple, reliable, effective and less invasive method for the fixation of metacarpal fractures although various types of devices have been developed to address some of the applications. An example of internal fixation by means of intramedullary implant for the fixation of fractured bones is U.S. Pat. No. 6,273,892B1 (Orbay et al.). This relates to an improved method and a related system for fixation of fractures of relatively small bones. It was particularly targeted at metacarpal fractures. Due to its location, splinting and casting it failed to maintain proper fracture reduction. Although the device provided fixation by insertion of fixation pins into the medullary canal of a fractured metacarpal, the effectiveness is limited by its weak torsional and longitudinal stabilities. In most cases, more than one fixation pin is required.

U.S. Pat. No. 6,533,788 B1 (Orbay) relates to a locking device and method for fixation pin stabilization within a fractured bone. This locking device includes a locking sleeve and a handle. This invention produces a device that provides torsional and longitudinal stability to the fixation pin and thereby to the bone through which the fixation pin extends. However, because this invention still adopts the idea of using a fixation pin for the intramedullary stabilization, it has relatively weak fixation, especially in the distal end of the pin where there is no locking device. In addition, other disadvantages such as, for example, frequent complication rates, the need for meticulous pin placement, adequate intraoperative evaluation of pin position, and patient compliance still remain.

Thus, there remains a need and desire for a bone fixation assembly that permits strong torsional and longitudinal fixation stability yet at the same time is less invasive, easy to manipulate, and flexible in application.

SUMMARY OF THE INVENTION

In accordance with a first preferred aspect there an intramedullary fixation device for fractures. The intramedullary fixation device compromises a core guide wire, and distal and proximal petal segments mountable on the core guide wire and being able to be moved towards each other. Each petal segment has multiple petals able to be expanded for gripping an internal wall of a medullary canal. The device also has expansion segments mountable on the core guide wire. Each expansion segment has a tapered engagement surface for engaging with and expanding the petals of the distal and proximal petal segments.

The core guide wire may have a leading end portion, a middle portion and a trailing end portion. The leading end portion may serve as a stopper for the distal petal segment. The middle portion may have external screw threading for engaging a threaded bore of the distal and proximal petals for threadingly mounting the distal and proximal petals on the middle portion. The trailing end portion may be for convenience of holding.

The intramedullary fixation device may further comprise a distal connecting segment with a counter-sink at one end to match the expansion segment, the other end being counter-bored.

The intramedullary fixation device may further comprise a proximal connecting segment having a counter-sink at one end to match the expansion segment, the other end having a protrusion.

The intramedullary fixation device may further comprise at least one optional segment with a protrusion at one end and a counter-bore at the other end.

The distal and proximal petal segments may be mounted on the core guide wire in an opposed relationship. The expansion segments may each have a chamfer to match a connecting segment.

Each petal segment may comprise a tapered internal surface for accommodating the expansion segment.

Accordingly to a second preferred aspect there is provided a multipiece assembly for intramedullary fixation comprising distal and proximal petal segments able to be expanded to grip an internal medullary canal wall so as to provide a stable fixation, an expansion segment for each of the distal and proximal petal segments for forcing the distal and proximal petal segments to be expanded upon tightening, and a core wire upon which the distal and proximal petal segments, and the expansion segments, are mounted, the core wire also being for effecting the tightening so as to form a rigid structure.

The core wire may have external screw threading, and there may be connecting segments and optional segments for enabling the multipiece assembly to be adjustable in length.

For both aspects the distal and proximal petal segments may each have an internal screw thread for mounting on the core guide wire and for controlling the axial position of the petal segment. Each petal segment may comprise a plurality of evenly distributed petals, and a tapered internal surface for accommodating the expansion segment.

According to a third preferred aspect there is provided a method for intramedullary fixation of a fracture, the method comprising:
  (a) passing a core guide wire with a distal petal segment mounted thereon into the medullary cavity such that the distal petal segment is in the medullary canal on a far side of the fracture;
  (b) passing a distal expansion segment along the core guide wire until it engages the distal petal segment;
  (c) passing a proximal expansion segment along the core guide wire;
  (d) passing a proximal petal segment along the core guide wire until it engages the proximal expansion segment on a near side of the fracture;
  (e) rotating the core guide wire to cause the distal and proximal petal segments to expand under the influence of the distal and proximal expansion segments such that the proximal and distal petal segment will securely engage the medullary cavity wall.

Rotation of the core guide wire may cause the distal and proximal petal segments to move towards each other.

After step (b) and before step (c):
  (f) a distal connecting segment may be passed along the core guide wire until it engages the distal expansion segment.

After step (f) and before step (c):
  (g) at least one optional segment may be passed along the core guide wire until it engages the distal connecting segment.

Alternatively after step (f) and before step (c):
  (g) a proximal connecting segment may be passed along the core guide wire until it engages the distal connecting segment. A proximal connecting segment may then be passed along the core guide wire until it engages the at least one optional portion.

The advantage of this device lies in that it is able to provide reliable torsional and longitudinal stability by means of the grip of the expanded petals onto the internal medullary wall. Another advantage of the device lies in that it is adjustable in length, which can accommodate the variation in metacarpal lengths of different patients or the variation in bone lengths when the device is extended to be applied in other similar bones.

Advantageously, due to the device being adjustable in length, the device may be used for any other fractures and for any long bone so long as the device is proportionally sized, i.e. adjustable to the appropriate length.

Other merits include the ease in manipulation—for both insertion and removal of the implant, and thus the fixation operation is less invasive due to the flexibility of the device. In order to minimize joint stiffness, the implant is designed to provide sufficient stability to the fracture fixation so the doctor may be able to order immediate appropriate rehabilitation care for the patient. The inwards compressive force of the fixation may aid fracture healing.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings:
FIG. 16 (a)-(l) shows the surgical insertion of the implant according to an embodiment of the invention;
and
FIG. 17 (a)-(f) shows the surgical removal of the implant according to an embodiment of the invention.

DETAILED DESCRIPTION OF THE PREFERRED EMBODIMENTS

While the present invention will be described more fully hereinafter with reference to the accompanying drawings, in which a particular embodiment is shown, it is to be understood at the outset that persons skilled in the art may modify the invention herein described while still achieving the favourable results of this invention. Accordingly, the description which follows is to be understood as a broad teaching directed to persons of skill in the appropriate arts and not as limiting upon the present invention.

Research on the anatomy of the hand, and the measurement on metacarpal bones, has shown that the length of metacarpal bone varies from 44.9 mm to 67.9 mm. As such, any implant must be able to accommodate changes in bone length. It is estimated that the medullary canal of the metacarpal bone is about half the diameter of the outer bone shell. The smallest diameter of the metacarpal bones has been found to be about 6.19 mm. Therefore, the maximum external diameter of any implant should be about 3.0 mm. The implant may withstand a load of 2 Kg applied to the tip of the finger. However, the dimensions and load will vary from patient-to-patient, and according to the bones concerned.

Figure 1:
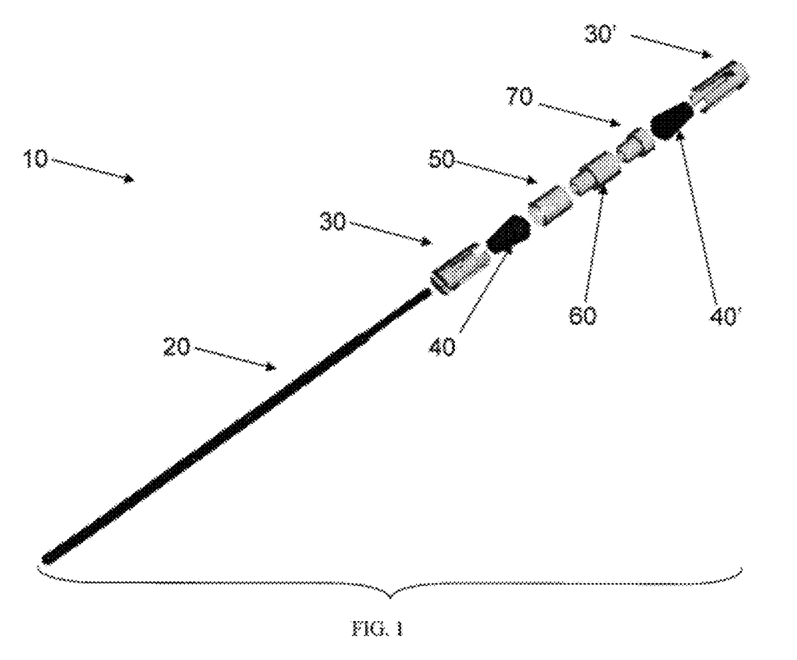
FIG. 1 is a perspective view of components of the fixation assembly illustrated in longitudinally spaced relation relative to each other.

Referring to the drawings, where like reference numerals refer to like parts throughout, FIG. 1 schematically illustrates a perspective view of components of the fixation assembly in longitudinally spaced relation relative to each other, in its entirety by reference numeral 10. As illustrated in FIG. 1, distal petal segment 30, distal expansion segment 40, distal connecting segment 50, optional segment 60, proximal connecting segment 70, proximal expansion segment 40', and proximal petal segment 30' are able to be mounted upon the core guide wire 20 in sequence and tightened to form a rigid rod fixation assembly 10. When tightened, the distal/proximal petal segments 30/30' will be expanded by the distal/proximal expansion segments 40/40' and will therefore grip onto the internal medullary wall of the bone, such as, for example, a metacarpal bone.

Figure 2:
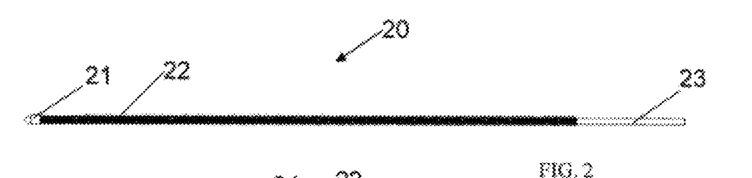
FIG. 2 is an elevational view of the core guide wire.
Figure 3:
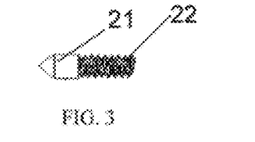
FIG. 3 is an enlarged elevational view of the head of core guide wire in FIG. 2.
Figure 4:
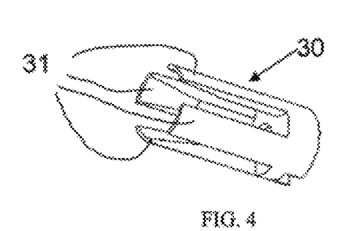
FIG. 4 is a perspective view of the distal/proximal petal.
Figure 5:
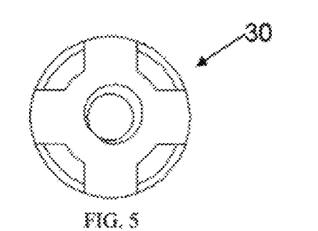
FIG. 5 is a left end view of the petal illustrated in FIG. 4.
Figure 6:
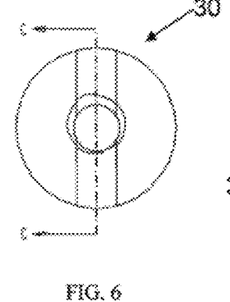
FIG. 6 is a right end view of the petal illustrated in FIG. 4.
Figure 7:
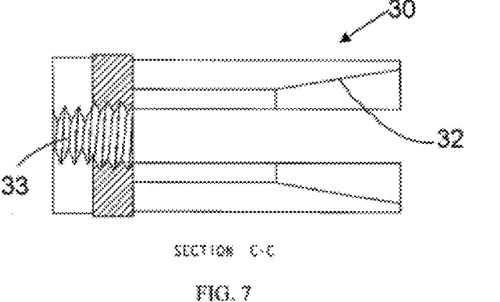
FIG. 7 is a sectional view taken along line C-C of FIG. 6.

FIG. 2 and FIG. 3 show the core guide wire 20. Core guide wire 20 may be fabricated from K-Wire that is commonly used in surgical procedures. The core guide wire 20 has a leading end portion 21, a middle portion with external screw threading 22, and a trailing end portion 23. The leading end portion 21 serves as a stopper for subsequent segments 30, 40, 50, 60, 70, 40', and 30', particularly the distal petal segment 30. The trailing end portion is for the convenience of holding. The core guide wire 20 will be introduced into the medullary canal to guide a reaming tool for enlarging the medullary canal, as well as for assembling and holding of the various segments.

FIGS. 4, 5, 6 and 7 illustrate the distal and proximal petal segments 30 and 30'. They are mounted on the core guide wire 20 in an opposed orientation. They are identical so that they can be used interchangeably to minimise any potential error due to wrong assembly. Screw threads 33 are formed in the bore of the petal segments 30, 30' for engaging the threaded portion 22 on the core guide wire 20 and to control the axial position of the petal 30. Therefore, as the core guide wire 20 is rotated, and as the distal 30 and proximal petal segments 30 face in opposite directions, they will be drawn towards each other by the interaction of the screw threads 22, 33. The four petals 31 of each of the petal segments 30, 30' will expand when the expansion segment 40 is pressed into the tapered portion 32, and thus will grip onto the internal wall of the medullary canal. This provides a stable fixation and prevents relative movement. When the distal 30 and proximal 30' petals expand while other components are being tightened, the petals 31 of both distal 30 and proximal 30' petals will be forced against the internal wall and thus provide a compressive force on the medullary canal wall. This force also produces a force by the distal 30 and proximal petal 30' towards each other by virtue of the interaction of the screw threads 22, 33. Due to the compressive force on the internal wall of the medullary canal and the drawing of the petal segments 30, 30' towards each other, this will slowly and slightly pull the fracture closed to help the fracture heal. The external surface of the petals 31 may be coated or textured to provide better grip. A proposed material for this component is stainless steel or titanium. The petals 31 are preferably evenly distributed around the petal segments 30, 30'.

Figure 8:
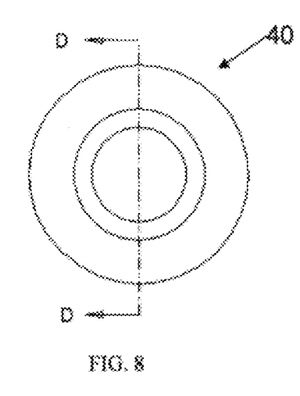
FIG. 8 is a small-size end view of the expansion segment illustrated in FIG. 1.
Figure 9:
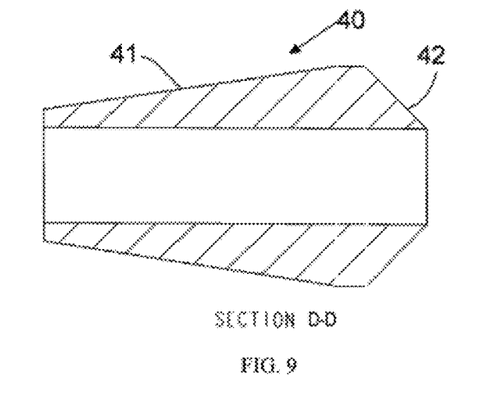
FIG. 9 is a sectional view taken along line D-D of FIG. 8.

FIGS. 8 and 9 illustrate the distal and proximal expansion segments 40 and 40', designed to be identical for use interchangeably and to minimise any potential error due to wrong assembly. The tapered surface 41 of the expansion segment is used to force open the petals 31 when all components are tightened together. The tapered surface 41 of the expansion segments 40, 40' is preferably polished to a fine finish for easy sliding into the petals 31. The other end of the expansion segments 40, 40' is a chamfer 42 to match the connecting segment 50 or 70. The chamfer 42 is to provide self-compliance when assembled and is preferably polished. A proposed material for this component is stainless steel or titanium.

Figure 10:
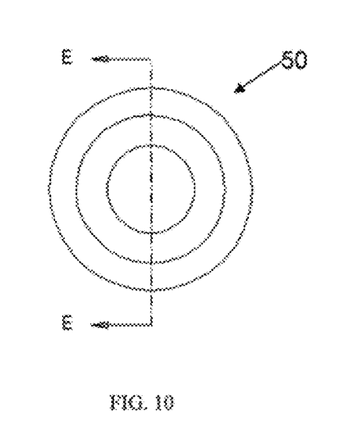
FIG. 10 is the right end view of the distal connecting segment illustrated in FIG. 1.
Figure 11:
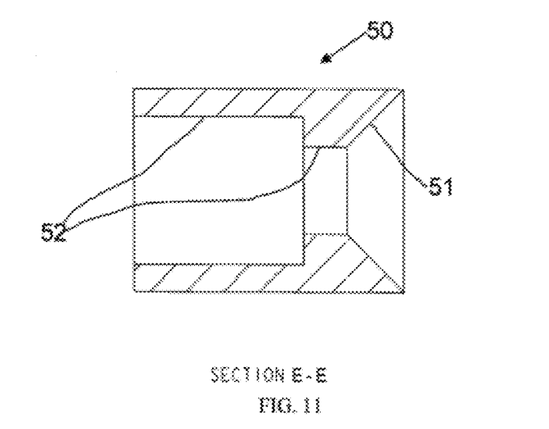
FIG. 11 is the sectional view taken along line E-E of FIG. 10.

FIGS. 10 and 11 illustrate the distal connecting segment 50, designed with a counter-sink 51 on one end that matches the chamfer 42 of the expansion segments 40, 40' so as to receive therein the chamfer 42 with self-compliance. Its opposite end is counter bored 52 to mate with the protrusion 61 of the optional segment 60 or the protrusion 72 of the proximal connecting segment 70 such that, when the assembly is tightened, a rigid structure results. The tolerances of the mating surfaces are preferably well controlled to assure proper functioning of the implant. A proposed material for this component is stainless steel or titanium.

Figure 12:
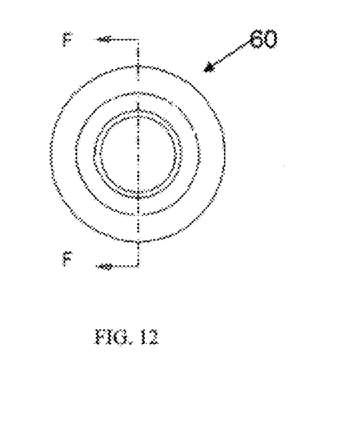
FIG. 12 is the left (small-size) end view of the optional segment illustrated in FIG. 1.
Figure 13:
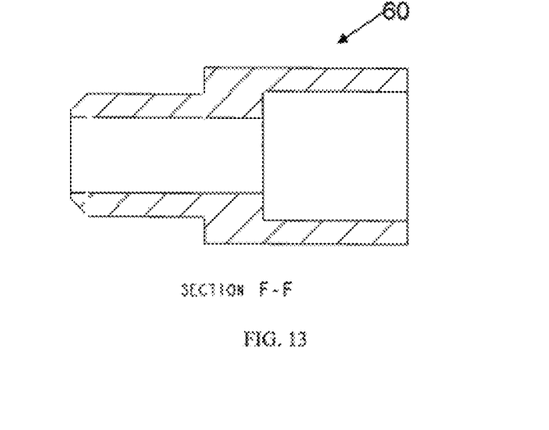
FIG. 13 is the sectional view taken along line F-F of FIG. 12.

FIGS. 12 and 13 illustrate the optional segment 60, designed with a protrusion 61 and a counter-bore 62 on each end. The counter-bore 62 is adapted to receive therein the protrusion 61 of an adjacent optional segment 60, or the protrusion 72 of the proximal connecting segment 70. Multiple pieces of the optional segments can be assembled to vary the length of the implant for catering to varying lengths of the relevant bones. While providing flexibility to vary the implant length, the optional segment is also flexible when loose, but becomes a rigid structure when tightened as the segments interlock with each other. The tolerance of the mating surfaces 61 and 62 are preferably well controlled to assure proper functioning of the implant. A proposed material for this component is stainless steel or titanium.

Figure 14:
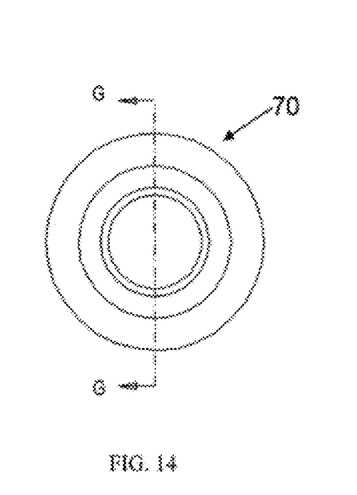
FIG. 14 is the left (small-size) end view of the proximal connecting segment illustrated ion FIG. 1.
Figure 15:
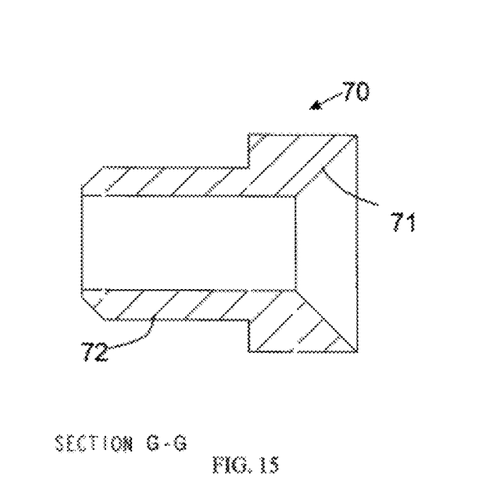
FIG. 15 is the sectional view taken along line G-G of FIG. 14.

FIGS. 14 and 15 illustrate the proximal connecting segment 70, designed with a countersink 71 on one end to match the expansion segment 40' with self-compliance; while its opposite end has a protrusion 72 that matches with the counterbore 62 of the optional segment 60 and the counterbore 52 of the distal connection segment such that when the assembly is tightened, a rigid structure results.

The protrusions 72 and 61 are preferably of the same external diameter, and the same axial length. The length of protrusions 72 and 61 should match the length of counterbores 62 and 52. The tolerance of the mating surfaces 71 and 72 should be well controlled to assure proper functioning of the implant. Examples of materials that can be used for this component are stainless steel and titanium.

All the components 40, 50, 60 70 and 40' have a central bore 43, 53, 63 and 73 respectively that is not threaded and is relatively smooth to enable them to be an easy, sliding fit on core guide wire 20.

When determining the components required for a fracture, the core guide wire 20 with its leading end portion and screw-threaded middle portion 22 is required, as are the distal 30 and proximal petal segments 30', and the distal and proximal expansion segments 40, 40'. The connecting segments 50, 70, and the optional segment(s) 60, may be used to adjust the axial length of the assembly.

The present invention also provides a method of intramedullary fixation of a fracture. The core guide wire 20, with the distal petal segment 30 mounted thereon adjacent the leading end portion 21, is inserted into the medullary cavity and engage its wall on the far side of the fracture. Distal expansion segment 40 is then passed over the core guide wire 20 until it engages the distal petal segment 30. The distal connecting portion 50 is then passed along the core guide 20 until it engages the distal expansion segment 40. If required, one or more optional segments 60 are then passed along core guide wire 20 until it or they engage the distal connecting segment 50. In the same manner, then follow the proximal connecting segment 70, proximal expansion segment 40' and, finally, the proximal petal segment 30'. The proximal petal segment 30' will engage the medullary cavity wall on the near side of the fracture.

The core guide wire 20 is rotated to cause the two petal segments 30, 30' to expand under the influence of the expansion segments 40, 40' respectively; and to move towards each other. This caused the petals 31 to expand to engage the medullary canal wall, and to force the fracture closed. When sufficiently tight, rotation of the core guide wire 20 can stop.

Although engaging projections and counterbores, and chamfers and countersinks are described, other mating structures for enabling one segment to cause the rotation of an adjacent segment may be used.

Example 1

Surgical Procedure for the Insertion of the Metacarpal Implant

Figure 16A:
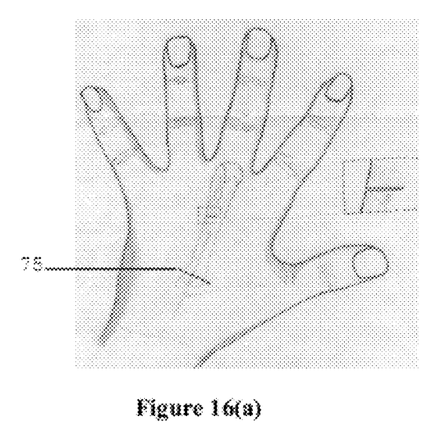

The surgical procedure for the insertion of the intra-medullary metacarpal implant into the medullary canal of a fractured metacarpal bone for stable bone fixation is illustrated in FIG. 16 and described as follows:

(a) A small incision 75 is made in the skin proximal to the metacarpal bone on the dorsal side of the palm, at the base of the fractured metacarpal bone. The example in FIG. 16(*a*) shows the $3^{rd}$ metacarpal bone.

Figure 16B:
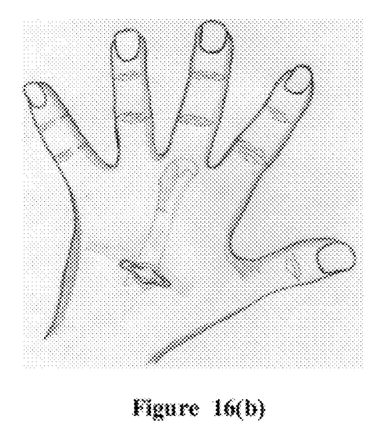

(b) The incision 75 is then stretched sufficiently to expose the base of the bone.

Figure 16C:
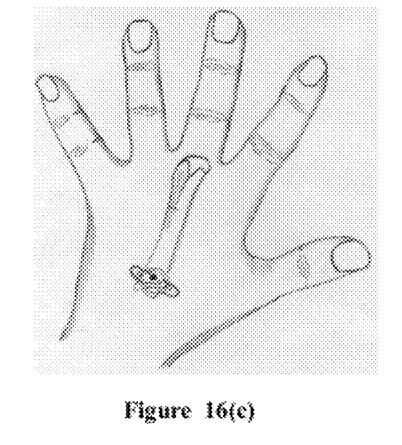

(c) An aur is inserted through the incision and is used to drill a small hole into the base of the metacarpal bone.

Figure 16D:
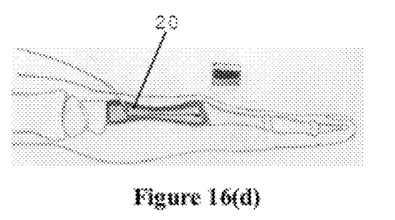

(d) The core guide wire (treaded K wire) 20 is inserted through the drilled hole into the intra-medullary canal. Insertion is guided by radiological assistance. The core guide wire 20 is passed through the fracture site up to the neck of the metacarpal bone.

Figure 16E:
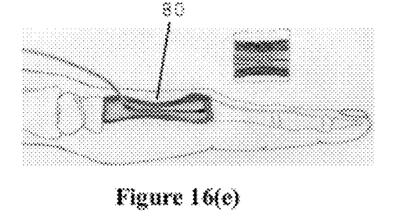

(e) A reamer 80 is introduced through the core guide wire 20 to bore a hole in the intra-medullary canal to the required diameter.

Figure 16F:
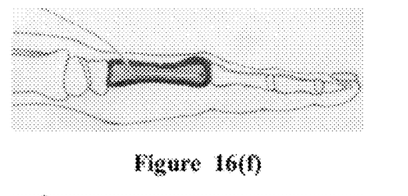

(f) The reamer 80 is then removed from the medullary canal making sure that the core guide wire 20 is still in its original position. The components of the intra-medullary implant are inserted into the bored hole in the following sequence (as shown in FIG. 1 and described above):
  (i) Distal Petal 30
  (ii) Distal Expansion Segment 40
  (iii) Distal Connecting Segment 50
  (iv) Optional Segment 60
  (v) Proximal Connecting Segment 70
  (vi) Proximal Expansion Segment 40'
  (vii) Proximal Petal 30'

Figure 16G:
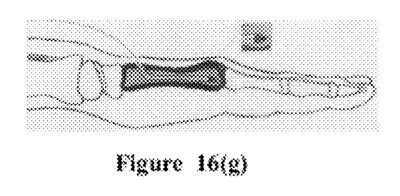

(g) The distal petal 30 is threaded along the core guide wire 20 until it reaches the end of the core guide wire 20.

Figure 16H:
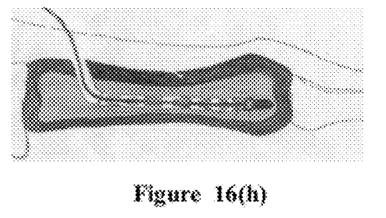

(h) The other components of the implant are inserted into the bored hole in the medullary canal of the metacarpal bone, along the core guide wire 20 in the sequence shown in step (g) and ending with the proximal petal 30'.

Figure 16I:
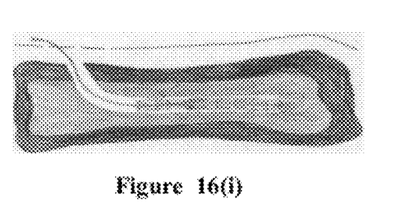

(i) The proximal petal 30' is then tightened with a petal screwdriver.

Figure 16J:
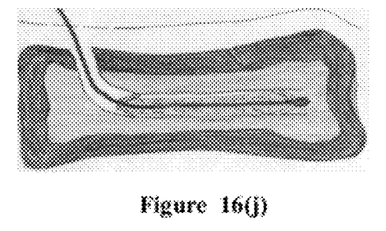

(j) Further tightening of the proximal petal 30' forces the four 'fingers' of the distal and proximal petals 30, 30' to flex outwards, expanding its free end. The 'fingers' include barbs that bite into the bored hole in the medullary canal of the fractured metacarpal bone when it is flexed outwards. Concurrently the distal and proximal petals 30, 30' compress the components between them. The flexed 'fingers' also exert a compressive force to move the fractured metacarpal bone closer together.

Figure 16K:
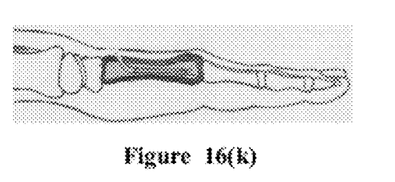

(k) The excess core guide wire 20 that is extending through the incision 75 is then cut off.

Figure 16L:
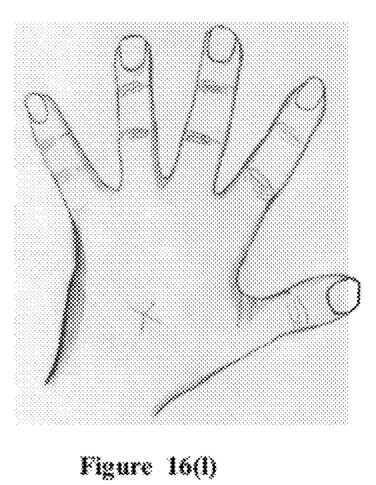

(l) The incision 75 is stitched up.

Example 2

Surgical Procedure for the Removal of the Metacarpal Implant

The need for removal of the implant arises when there are surgical complications and the implant needs to be reinserted or alternate fracture reduction methods may be required.

Figure 17A:
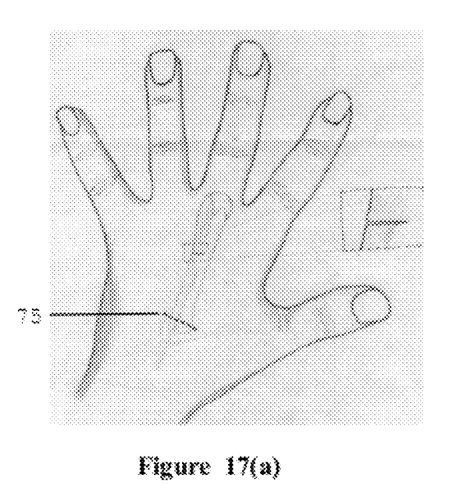

The surgical procedure for the removal of the intra-medullary metacarpal implant is illustrated in FIG. 17 and described as follows:

(a) The stitches are removed from the incision 75 to re-expose the bone.

Figure 17B:
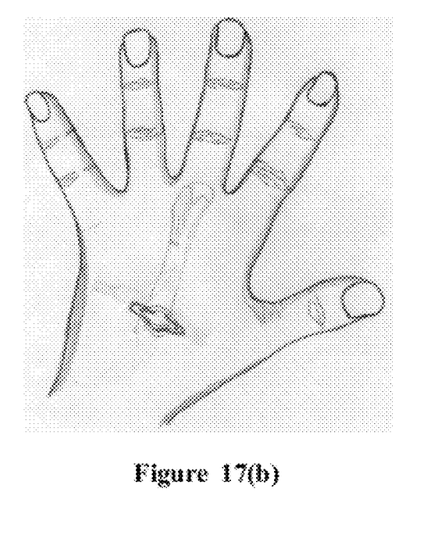
Figure 17C:
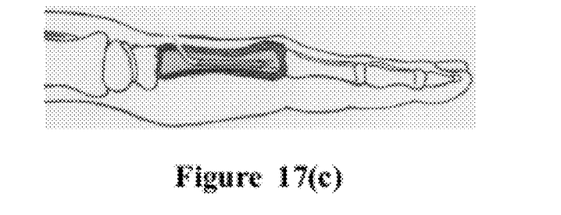

(b) The incision 75 is stretched sufficiently to expose the base of the bone (c) The cut end of the core guide wire 20 is located.

Figure 17D:
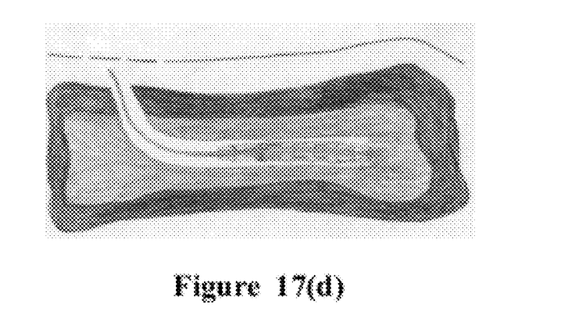

(d) The proximal petal 30' is loosened and removed with a petal screwdriver.

Figure 17E:
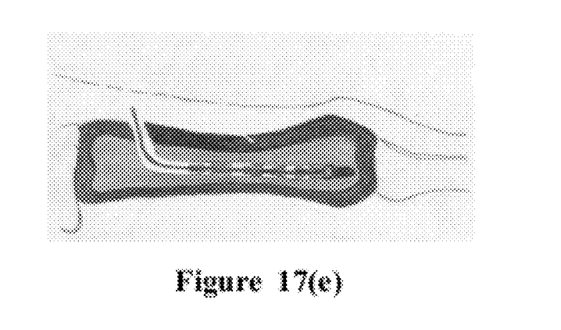

(e) The core guide wire 20 is pulled and pushed with a pair of pliers; at the same time, a clockwise and counter-clockwise twist is applied on the core guide wire 20. The motion is repeated where necessary. These series of motion will loosen the components and allows the fingers on the distal petal 30 to contract, releasing its grip on the medullary canal wall.

Figure 17F:
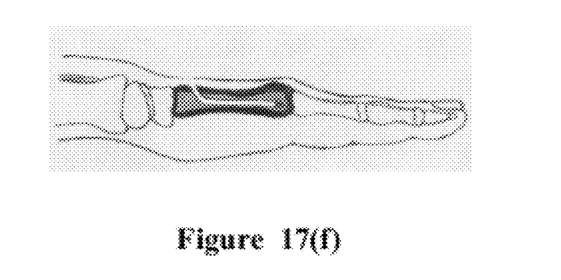

(f) The implant is gently pulled out when the components have sufficiently loosen in the medullary canal.

The implant being adjustable in length, the implant may be used for any other fractures and for any long bone so long as the implant is proportionally sized, i.e. adjustable to the appropriate length.

Whilst there has been described in the foregoing description preferred embodiments of the present invention, it will be understood by those skilled in the technology concerned that many variations or modifications in details of design or construction may be made without departing from the present invention.

The invention claimed is:

1. A method for intramedullary fixation of a fracture with an intramedullary fixation device comprising:
  (a) a core guide wire;
  (b) distal and proximal petal segments mountable on the core guide wire and being able to be moved towards each other, each petal segment having multiple petals able to be expanded for gripping an internal wall of a medullary canal;
  (c) distal and proximal expansion segments mountable on the core guide wire, each expansion segment having a tapered engagement surface for engaging with and expanding the petals of the distal and proximal petal segments, with the distal expansion segment having a chamfer;
  (d) a distal connecting segment with a counter-sink at one end to mate with the chamfer of the distal expansion segment, the other end being counter-bored; and
  (e) a proximal connecting segment having a counter-sink at one end to mate with the proximal expansion segment, the other end of the proximal connecting segment having a protrusion to mate with the counter-bored end of the distal connecting segment, with the method comprising:

(a) passing the core guide wire with the distal petal segment mounted thereon into the medullary cavity such that the distal petal segment is in the medullary canal on a far side of the fracture;

(b) passing the distal expansion segment along the core guide wire until it engages the distal petal segment;

(c) passing the distal connecting segment along the core guide wire until it engages the distal expansion segment;

(d) passing at least one optional additional segment along the core wire until it engages the distal connecting segment;

(e) passing the proximal expansion segment along the core guide wire;

(f) passing the proximal petal segment along the core guide wire until it engages the proximal expansion segment on a near side of the fracture; and (g) rotating the core guide wire to cause the distal and proximal petal segments to expand under the influence of the distal and proximal expansion segments such that the proximal and distal petal segments will securely engage the medullary cavity wall.

2. The method of claim 1, wherein the rotation of the core guide wire causes the distal and proximal petal segments to move towards each other.

3. The method of claim 2, wherein the core guide wire comprises a leading end portion, a middle portion, and a trailing end portion and wherein the leading end portion serves as a stopper for the distal petal segment.

4. The method of claim 3, wherein the middle portion has a external screw thread for engaging a threaded bore of the distal and proximal petal segments for threadingly mounting the distal and proximal petal segments on the middle portion.

5. The method of claim 3, wherein the trailing end portion is configured for convenience of holding.

6. The method of claim 2, further comprising providing the core guide wire with an external screw thread, and providing the distal and proximal petal segments each with an internal screw thread for mounting on the core guide wire for controlling an axial position of the distal and proximal petal segment.

7. The method of claim 2, wherein the distal and proximal petal segments are each provided with a plurality of evenly distributed petals, and a tapered internal surface for accommodating the expansion segments.

8. The method of claim 2, further comprising mounting the distal and proximal petal segments on the core guide wire in an opposed relationship.

9. The method of claim 1, wherein after step (d) and before step (e):

(ii) a proximal connecting segment is passed along the core guide wire until it engages the at least one optional segment.

10. The method of claim 1, wherein the at least one additional segment is provided and is engaged between the distal connecting segment and the proximal connection segment for enabling the intramedullary segment to be adjustable in length.

11. The method of claim 1, further comprising providing at least one additional segment engaged between the distal connecting segment and the proximal connection segment for enabling the intramedullary segment to be adjustable in length; and passing the additional segment along the core wire until it engages the distal connecting segment as recited in step (d).

12. The method of claim 11, further comprising providing the at least one additional segment with a protrusion at one end and a counter-bore at the other end.

* * * * *